US012326437B2

(12) United States Patent
Locklear et al.

(10) Patent No.: US 12,326,437 B2
(45) Date of Patent: Jun. 10, 2025

(54) ELEMENTAL SULFUR ANALYSIS IN FLUIDS

(71) Applicant: CONOCOPHILLIPS COMPANY, Houston, TX (US)

(72) Inventors: Jay Locklear, Houston, TX (US); Clinton Crowe, Houston, TX (US)

(73) Assignee: CONOCOPHILLIPS COMPANY, Houston, TX (US)

( * ) Notice: Subject to any disclaimer, the term of this patent is extended or adjusted under 35 U.S.C. 154(b) by 98 days.

(21) Appl. No.: 18/335,664

(22) Filed: Jun. 15, 2023

(65) Prior Publication Data

US 2023/0324361 A1    Oct. 12, 2023

Related U.S. Application Data

(62) Division of application No. 17/062,281, filed on Oct. 2, 2020, now Pat. No. 11,719,684.

(60) Provisional application No. 62/910,501, filed on Oct. 4, 2019.

(51) Int. Cl.
*G01N 33/28*     (2006.01)
*G01N 21/75*     (2006.01)

(52) U.S. Cl.
CPC ........... G01N 33/287 (2013.01); G01N 21/75 (2013.01); *Y10T 436/109163* (2015.01); *Y10T 436/188* (2015.01)

(58) Field of Classification Search
CPC .......... G01N 33/287; G01N 2001/2893; Y10T 436/188; Y10T 436/109163
See application file for complete search history.

(56) References Cited

U.S. PATENT DOCUMENTS

| | | | |
|---|---|---|---|
| 5,160,045 A | 11/1992 | Falkiner et al. | |
| 5,199,978 A | 4/1993 | Poirier et al. | |
| 5,674,378 A | 10/1997 | Kraemer et al. | |
| 6,875,414 B2 | 4/2005 | Sundaram et al. | |
| 8,524,071 B2 | 9/2013 | Landau et al. | |
| 8,535,422 B2 | 9/2013 | Via et al. | |
| 9,988,270 B2 | 6/2018 | Hojjatie et al. | |
| 10,564,142 B2 | 2/2020 | Oduro | |
| 2001/0051751 A1* | 12/2001 | Bennett | C07C 321/14 568/21 |
| 2013/0149788 A1 | 6/2013 | Sacks et al. | |
| 2021/0102932 A1* | 4/2021 | Locklear | G01N 21/75 |

OTHER PUBLICATIONS

Deng, T. et al. "Phase transfer catalysis of disproportionation of elemental sulfur," Wuji Huaxue 3(4) 128-131 (1987), SciFinder Abstract and Substances only. (Year: 1987).*
Cheng, H.; Hous, F.; Li, C.; Zheng, S.(2017) "Analysis and equilibrium constant of polysulfides in desulfurization solution." Chemical Engineering Transactions, 61, 1927-1932.
Vaccari, G.; Silva, R. (1972) "Spectrophotometric microdetermination of elemental sulfur." Chmica e l'Industria, vol. 54(8), 695-697.
Bartlett, J. K.; Skoog, D. A. (1954) "Colorimetric determination of elemental sulfur in hydrocarbons." Analytical Chemistry, vol. 26(6), 1008-1011.
Tartar, H. V. (1913) "On the reaction between sulfur and potassium hydroxide in aqueous solution." JACS, 35, 11, 1741-1747.
Danielsson, L.-G.; Chai, X-S.; Behm, M.; Renberg, L. (1996) "UV characterization of sulphide-polysulphide solutions and its application for process monitoring in the electrochemical production of polysulphides." Journal of pulp and paper science, vol. 22(6), J187-J191.
Urbanski, T. (1962) "New colour reactions of elemental sulphur and carbon disulphide." Talanta, vol. 9, 799-800.
Skoog, D. A.; Bartlett, J. K.(1955) "Titration of elemental sulfur with solutions of sodium cyanide." Analytical Chemistry, 27, 369-371.
ASTM D2622-16 "Standard test method for sulfur in petroleum products by wavelength dispersive X-ray Fluorescence Spectrometry."
ASTM D4294 "Standard test method for sulfur in petroleum and petroleum products by energy dispersive X-ray Fluorescence spectrometry.", (2008).
ASTM D5453-19a "Standard test method for determination of total sulfur in light hydrocarbons, spark ignition engine fuel diesel engine fuel, and engine oil by ultraviolet fluorescence.", (2019).
ASTM D5623-19 Standard test method for sulfur compounds in light petroleum liquids by gas chromatography and sulfur selective detection, (2019).
ASTM D129-18 Standard test method for sulfur in petroleum products (general high pressure decomposition device method), (2018).
ASTM D4292-17 "Standard test method for determination of vibrated bulk density of calcined petroleum coke.", (2017).

* cited by examiner

*Primary Examiner* — Jennifer Wecker
*Assistant Examiner* — Michelle Adams
(74) *Attorney, Agent, or Firm* — Boulware & Valoir PLLC

(57)    ABSTRACT

Robust methods for quantitating the amount of elemental sulfur in a fluid whereby a caustic solution is mixed with the fluid, and the elemental sulfur present in the fluid reacts to form a colored solution that can be compared to a series of standards. The methods can be performed in a laboratory or the field and allow for real time feedback. Once the concentration of the elemental sulfur is known, appropriate methods of treatment can proceed. Test kits for performing the methods in the field are also described.

10 Claims, 2 Drawing Sheets

ELEMENTAL SULFUR ANALYSIS IN FLUIDS

PRIOR RELATED APPLICATIONS

This invention is a divisional application of Ser. No. 17/062,281, filed on Oct. 2, 2020U, (U.S. Pat. No. 11,719,684), which claims priority to U.S. Application No. 62/910,501, filed on Oct. 4, 2019, and incorporated by reference in its entirety herein for all purposes.

FEDERALLY SPONSORED RESEARCH STATEMENT

Not applicable.

REFERENCE TO MICROFICHE APPENDIX

Not applicable.

FIELD OF THE DISCLOSURE

The disclosure relates generally to methods of determining the concentration of elemental sulfur in hydrocarbons.

BACKGROUND OF THE DISCLOSURE

Hydrocarbon fluids and gases often contain a variety of sulfur compounds, including elemental sulfur. When sulfur is present in concentrations of 1 percent or more by weight, the hydrocarbon is characterized as "sour" and concentrations of 0.5 percent or less are "sweet" hydrocarbons. It is well known that elemental sulfur and other sulfur compounds contained in hydrocarbon streams are corrosive and damaging to metal equipment, particularly copper and copper alloys. The sulfur has a particularly corrosive effect on equipment such as brass valves, gauges and in-tank fuel pump copper commutators.

Even after processing, sulfur and sulfur compounds may be present in a hydrocarbon stream in varying concentrations, and additional contamination may take place as a consequence of transporting the hydrocarbon stream through pipelines containing residual sulfur contaminants from previous transportation of sour hydrocarbon streams. This is problematic because it increases sulfur dioxide ($SO_2$) emissions when fossil fuels are combusted, and poisons catalysts utilized in the refining process.

To monitor the amount of elemental sulfur present in crude, intermediates and final products, the fluids are analyzed in a lab setting by gas or liquid chromatographic methods with various detectors or x-ray fluorescence (XRF), or in the field through various 'portable' methods involving toxic chemicals.

For the chromatographic methods, the elemental sulfur is separated from other molecules based on interactions with a stationary phase in the separation column, before being analyzed with a detector. While the detection limit for these instruments is in the ppm to ppb range, the portability of these methods is extremely low and the capital cost for the chromatographic instruments are high.

XRF relies on the emission of characteristic "secondary" (or fluorescent) x-rays from sulfur in fluid that has been excited by bombarding with high-energy X-rays or gamma rays. XRF analysis has higher concentration detection limits than chromatographic methods and is not specific to elemental sulfur, meaning it will detect all sulfur material as one species. Additional disadvantages of XRF include requirements of special permits because of the radiation, high capital costs, and limited portability.

Similar spectroscopy-based tests include ASTM D2622, which determines Wavelength Dispersive X-ray Fluorescence Spectrometry, and ASTM D4294-16e1, which uses Energy Dispersive X-ray Fluorescence Spectrometry. In each case, the equipment is expensive and not portable.

Another test is ASTM D5453-93. In this method, a measured quantity of the hydrocarbon sample is injected into a pyrotube and oxidized in a rich pure oxygen stream in the combustion zone at approximately 1000° C. where it is converted into $CO_2$, $SO_2$ and $H_2O$. Once the gases exit the combustion zone, they are passed through a semipermeable Nafion® membrane where the water is quantitatively removed. The gases enter the sulfur reaction chamber where they are exposed to an UV light. The $SO_2$ molecules absorb the radiation to become excited, and the relaxation releases a secondary energy that is captured by a Photo Multiplier Tube, amplified, processed and recorded. The signal obtained is proportional to the total sulfur content of the original sample and is not specific to elemental sulfur. However, this method requires complex, expensive equipment and is not suitable for well pad or field use.

Yet another test is a Gas Chromatography (GC) chemiluminescence test, described in ASTM D5623, which uses GC combined with a Pulsed Flame Photometric Detector (PFPD). This method is used to identify organic sulfur compounds in some of the lighter feedstocks with a boiling point of 230° C. or lower at atmospheric pressure. Again, this type of sophisticated equipment is expensive and not well suited for field use.

Another ASTM test for sulfur is ASTM D129-18. This is a bomb test method for determination of the amount of sulfur in petroleum products with low volatilities and entails oxidizing samples by combustion and determining the amount of sulfur is by gravimetry.

Portable methods do exist to allow for elemental sulfur detection in the field. While portable, these methods use highly toxic chemicals, which adds additional steps to the analysis process and presents significant hazards to workers. For example, a polarographic technique use a mercury electrode for detecting the elemental sulfur in the presence of cyanide.

There is also a turbidimetric technique using barium chloride to form a barium sulfate white precipitate. The amount of precipitate so formed, either measured with a turbidity meter or a colorimeter, generally ranges from to about 15.0 mg/liter. However, this method only detects sulfate, not other forms of sulfur.

US20130149788 teaches a method whereby the elemental sulfur contained in the test sample are converted into volatilized hydrogen sulfide using benign reagents, such as dithiothreitol (DTT), dithioerythritol (DTE), glutathione, cysteine, tris(2-carboxyethyl) phosphine (TCEP), and the like. The amount of volatilized hydrogen sulfide is then determined. Typically, the $H_2S$ is reacted with a transition metal salt, forming an insoluble darkly colored precipitate. The amount of precipitate formed is proportional to the amount of elemental sulfur present in the original sample. $H_2S$ is of course, very toxic, making this method less desirable. US20190101519 also proceeds via a $H_2S$ conversion.

U.S. Pat. No. 5,199,978 teaches a method of removing sulfur from petroleum fluids, whereby sulfur-containing fluids are mixed with an inorganic caustic material, an alkyl alcohol and an organo-mercaptan or sulfide compound capable of reacting with sulfur to form a fluid-insoluble polysulfide salt reaction product at ambient reaction temperatures. The treated fluid is then contacted with an adsorbent or filtered to remove the insoluble salt leaving a product of very low residual sulfur content. However, a field-based assay for sulfur quantification based on this invention has not yet been developed.

Thus, what is needed in the art is a simple, safe, and portable method for determining the concentration of elemental sulfur in various fluids. The method is preferably robust and reliable in both a laboratory setting or in the field.

SUMMARY OF THE DISCLOSURE

The present disclosure provides novel methods of quantitating the amount of elemental sulfur in a fluid, both in a laboratory setting and in the field. Specifically, a caustic solution is mixed with a sample fluid containing elemental sulfur, wherein the elemental sulfur reacts with the caustic to form a colored sample solution. The presence of other sulfur species such as hydrogen sulfide, and disulfide do not react with the caustic, and do not cause interference on the time scale of the analysis. Test kits and protocols for using the methods and/or kits in the field are also described.

The color of the sample solution varies based on the composition of the sample fluid, and can be from near UV through the visible spectrum. This allows the sample solutions to be compared, using Ultraviolet-Visible (UV-Vis) spectroscopy, to a series of standards comprising known amounts of elemental sulfur in the same fluid matrix that has been reacted with the same caustic solution to determine the concentration of elemental sulfur in the sample solutions. This flexibility in the analysis method creates a robust method that is capable of being performed in the field, near the sampling site, or in a laboratory, with equal precision.

The methods can be used to determine the amount of elemental sulfur in any fluid where the presence of the elemental sulfur is detrimental to the performance of the fluid and/or the equipment in contact with the fluid. This can include both liquids and solids. Exemplary hydrocarbon fluids include refined hydrocarbon streams that are liquid at room temperature (gasoline, jet fuel, kerosene), unrefined liquid hydrocarbon (such condensates, black oils), and hydrocarbons streams that are solid at room temperature (waxes, asphalt) but can be solubilized into liquid hydrocarbons, as well as oilfield solvents (e.g. methanol, monoethylene glycol, triethylene glycol, tetraethylene glycol). Produced water or other waters, including water-based treatment fluids, can be analyzed directly or can be extracted with a hydrocarbon solvent to concentrate the elemental sulfur content above lower detection limits.

Sensitivity of the described methods are dependent on the sample fluid matrix, with more error being associated with the presence of background material that absorbs in the scanned wavelengths. However, the method provides reasonable sensitivity (i.e. 3× background value) from 5-20000 mg/L of elemental sulfur with about a 3-10% error (higher error occurring at the lower concentration limit). Better sensitivity is seen when using high end laboratory quality UV-Vis spectrometer; however, field instrumentation is acceptable for some applications. Further, techniques such as background subtraction can be used to reduce the error, particularly for samples with low sulfur concentrations.

In more detail, sample fluids containing elemental sulfur are reacted with a caustic chemical such as a base to form a colored solution. For spectroscopic evaluation, all parts of this reaction mixture must stay in solution. As such, the caustic chemical is generally dissolved in a solvent, such as an organic solvent, that does not precipitate solids in the sample fluid. The caustic (i.e. strong base) reacts with the elemental sulfur while the organic solvent maintains the solubility of the sample fluid and the base in the reaction solution. Exemplary caustics include any strong base, such as sodium hydroxide (NaOH), potassium hydroxide (KOH), and tetrabutylammonium hydroxide 30-hydrate (TBAOH), tetramethylammonium hydroxide, tetraethylammonium hydroxide, lithium hydroxide, cesium hydroxide, magnesium hydroxide, as well as methoxides, ethoxides, and propoxides. Exemplary organic solvents for the caustic include methanol, ethanol, isopropanol, toluene, hexane, benzene, dioxane, chloroform, diethyl ether, and combinations thereof. In some embodiments, the caustic solution is a caustic base that has been added to an alcohol to form a caustic alcohol. Alternatively, a mixture of an alcohol and a hydrocarbon solvent are used to solubilize the base.

The ratio of the caustic solution to the sample fluid is at least 5:1, or 2:1, or 10:1, and can be as high as at least 500:1. Alternatively, about 10 mL of the caustic solution is added to about 0.025 mL to about 0.05 mL of the sample fluid. The sample/caustic mixture is allowed to react for almost one minute, resulting in a colored reaction solution. Without being tied to a particular method of reaction, it is believed that cyclic allotropes of elemental sulfur are the color generating species in the sample fluid. This explains why the presently described methods are specific to elemental sulfur, whereas other sulfur-containing species such as hydrogen sulfide, and disulfide do not react with the caustic alcohol.

After about one minute of mixing, the reaction sample can be analyzed by scanning the 300-700 nm range with the UV-Vis spectrometer. The intensity of the color will begin to dissipate with minutes of the sulfur and caustic. For precise, reliable, and consistent measurements, absorbance of the reaction solutions should be taken within 15 minutes of the addition of the caustic solution. Preferably, the absorbance is taken within 5 minutes, and most preferably taken at the one-minute mark after the addition of the caustic solution. However, measurements may also be taken up to 60 minutes after the addition of the caustic solution for most sample fluids. While yet other samples can be measured in less than one minute, such a short period can result in inconsistent mixing and rushing to transfer fluids to the analysis chamber. Thus, it was found that measurements taken between 1 and 15 minutes consistently resulted in precise and reliable measurements.

In addition to precise and reliable measurements, an advantage of starting the analysis at exactly 60 seconds after the addition of the caustic solution is the lack of precipitation. Spectroscopic evaluation requires complete solubility of all components in the solution, as precipitated particles interfere with the absorption signal. Some caustic-organic solvent mixtures can absorb carbon dioxide from air, thus forming potassium carbonate. Potassium carbonate may have solubility issues in some organic solvents and can form precipitates quite quickly. Scanning the samples starting at 60 seconds after the addition of the caustic solution is quick enough to avoid such precipitates. However, if longer time is needed, or if samples are to be observed over days to months, any formed precipitates may be filtered out or allowed to settle before analysis.

The US-Vis is a high quality, laboratory instrument. However, portable, field UV-Vis instrumentation can also be used, allowing for onsite quantification of the elemental sulfur. Examples of field instruments include the Hach DR1900 portable spectroscopy unit, the Vernier UV-Vis Spectrophotometer, and the Ocean Optics USB4000-UV-Vis.

The absorbance of the sample reaction solution, typically at its peak absorbance but not always, is compared to the absorbance of at least 3 different standard solutions with known amounts of elemental sulfur at the same wavelength(s). The standards have the same matrix as the sample fluid to provide a reliable comparison, and can be prepared by any methods known in the art. The most common method is to create standards by diluting the sample fluid in an elemental sulfur-free hydrocarbon matrix, such as toluene or xylene. These diluted samples are then spiked with known amounts of elemental sulfur. The standard solutions can then be mixed with the same caustic solution, reacted for about one minute, and analyzed. Alternatively, the matrix of the sample fluids and standards can be matched using the standard addition approach.

In some embodiments, the sample solutions may also need to be diluted in a hydrocarbon solvent (e.g. toluene or xylene) to maintain an absorbance value under 1.3, which equates to 5% light transmission. Values higher than 1.3 decay on a log scale, increasing errors. Thus, the samples solutions may need to be diluted using well-known methods to maintain an absorbance level below 1.3.

In other embodiments, modifications to the UV-Vis analysis may be needed to account for low levels of elemental sulfur (less than or equal to 100 ppm) or higher levels (above 100 ppm) of elemental sulfur. For lower levels of elemental sulfur, the cuvette size can be increased to obtain a path length of about 50 mm and/or background subtraction techniques can be used to remove the signal contribution from the sample matrix. For higher concentrations, smaller cuvette can be used to obtain path lengths in the range of 10 mm or less.

Once the concentration of elemental sulfur is known, treatment methods can be customized for the system and/or sample fluid in question.

The present methods include any of the following embodiments in any combination(s) of one or more thereof:

A method of determining the amount of elemental sulfur in a fluid comprising adding a caustic solution to a sample of a fluid containing elemental sulfur, wherein the caustic solution reactions with the elemental sulfur to form colored reaction products. The absorbance of the reaction products is then obtained and compared with the absorbance of a series of standard solutions of known elemental sulfur concentration. The concentration of the elemental sulfur in the sample is then determined based on the absorbance comparison.

A method of determining the amount of elemental sulfur in a fluid comprising adding a caustic solution to a fluid sample of a refined or unrefined hydrocarbon liquid stream containing elemental sulfur, wherein the caustic solution reactions with the elemental sulfur to form colored reaction products. The absorbance of the reaction products is then obtained and compared with the absorbance of a series of standard solutions of known elemental sulfur concentration. The concentration of the elemental sulfur in the sample is then determined based on the absorbance comparison.

Any of the herein described methods, wherein the comparing step comprises using UV-Vis spectroscopy to obtain the absorbances of both the reaction products and the standard solutions. The UV-Vis spectrometer can scan from 300-700 nm or can scan select wavelengths.

Any of the herein described methods, wherein the caustic solution is a caustic alcohol or a caustic alcohol/hydrocarbon solvent mixture.

Any of the herein described methods, wherein the caustic solution contains a strong base in at least one organic solvent, or a strong base/organic solvent/hydrocarbon solvent mixture. Any of the herein described methods, wherein the organic solvent in the caustic solution is an alcohol.

Any of the herein described methods, wherein the caustic solution comprises a potassium hydroxide, methanol, and toluene.

Any of the herein described methods, wherein the caustic solution comprises a tetrabutylammonium hydroxide 30-hydrate, isopropanol, and toluene.

Any of the herein described methods, wherein the caustic solution comprises tetrabutylammonium hydroxide 30-hydrate in an organic solvent. The concentration of the tetrabutylammonium hydroxide 30-hydrate in the caustic solution can be between about 0.0001 and about 0.1 M, or between about 0.01 and 0.1M. Alternatively, the concentration of the tetrabutylammonium hydroxide 30-hydrate in the caustic solution can be between about 0.0001 in a 19.4 M.

Any of the herein described methods, wherein the concentration of caustic in the caustic solution is between about 0.0001 and about 19.4 M.

Any of the herein described methods, wherein the volume ratio of the caustic solution to the sample is 5:1 or 2:1 or 10:1. Alternatively, any of the above methods wherein 10 mL of a caustic solution is added to about 0.5 mL of the sample.

Any of the herein described methods, wherein the fluid is selected from a group comprising gasoline, jet fuel, waxes, kerosene, condensates, black oils, solid hydrocarbons that can be solubilized in liquid hydrocarbons, methanol, monoethylene glycol, triethylene glycol, tetraethylene glycol, produced water, and combinations thereof, or a gas produced from a reservoir.

Any of the herein described methods, wherein the fluid is translucent.

Any of the herein described methods, wherein all steps are performed at the site of the fluid sampling.

Any of the herein described methods, further comprising the step of treating the fluid to convert the elemental sulfur to insoluble sulfur products and removing the insoluble sulfur products from the fluid.

Any of the herein described methods, further comprising the step of treating equipment surfaces in contact with the fluid to prevent corrosive damage from the elemental sulfur.

Any of the herein described methods, wherein the caustic chemical is a strong base selected from a group consisting of NaOH, KOH, tetrabutylammonium hydroxide, tetramethylammonium hydroxide, tetraethylammonium hydroxide, lithium hydroxide, cesium hydroxide, magnesium hydroxide, lithium methoxide, sodium methoxide, potassium methoxide, lithium ethoxide, sodium ethoxide, potassium ethoxide, lithium propoxide, sodium propoxide, and potassium propoxide.

Any of the herein described methods, wherein the organic solvent is polar.

Any of the herein described methods, wherein the organic solvent is selected from a group consisting of methanol, ethanol, isopropanol, butanol, DMSO, DMF, propylene carbonate, dioxane, chloroform, diethyl ether, toluene, or xylene.

Any of the herein described methods, wherein the hydrocarbon solvent is selected from a group consisting of gasoline, diesel, kerosene, hexane, benzene, toluene, xylene, heavy aromatic naphtha, mixtures of naphtha and naphthalene, and naphthalene.

A test kit for determining the amount of elemental sulfur in a fluid, wherein the test kit has a storage container comprising a first container containing a known amount of a caustic chemical; a second container containing a hydrocarbon solvent; a third container containing an organic solvent; a fourth container containing a known amount of elemental sulfur; and a set of instructions for using the caustic chemical, the hydrocarbon solvent, the organic solvent, and the elemental sulfur to determine the amount of elemental sulfur in a fluid.

A test kit for determining the amount of elemental sulfur in a fluid, wherein the test kit comprises a storage container comprising a first container containing a caustic solution having a known amount of a caustic chemical and a known amount of an organic solvent; a second container containing a hydrocarbon solvent; a third container containing a known amount of elemental sulfur; and a set of instructions for using the caustic solution, the hydrocarbon solvent, and the elemental sulfur to determine the amount of elemental sulfur in a fluid.

A test kit comprising a storage container having a) a first container containing a solution having a known amount of a caustic chemical; b) a second container containing a known amount of a hydrocarbon solvent; c) a third container containing a known amount of an alcohol; d) a fourth container containing a known amount of elemental sulfur; and e) a set of instructions for using said caustic, said hydrocarbon solvent, said alcohol, and said elemental sulfur to determine the amount of elemental sulfur in a fluid.

A test kit for determining the amount of elemental sulfur in a fluid, wherein the test kit comprises a storage container comprising a first container containing a caustic solution having a known amount of a caustic chemical and a known amount of an alcohol; a second container containing a hydrocarbon solvent; a third container containing a known amount of elemental sulfur; and a set of instructions for using the caustic solution, the hydrocarbon solvent, and the elemental sulfur to determine the amount of elemental sulfur in a fluid.

A test kit for determining the amount of elemental sulfur in a fluid, wherein the test kit comprises a storage container comprising a first container containing a caustic solution having a known amount of a caustic chemical, a known amount of an organic solvent, and a known amount of a hydrocarbon solvent; a second container having a known amount of elemental sulfur; and a set of instructions for using the caustic solution and the elemental sulfur to determine the amount of elemental sulfur in a fluid.

A test kit for determining the amount of elemental sulfur in a fluid, wherein the test kit comprises a storage container comprising a first container containing a caustic solution having a known amount of a caustic chemical, a known amount of an alcohol, and a known amount of a hydrocarbon solvent; a second container having a known amount of elemental sulfur; and a set of instructions for using the caustic solution and the elemental sulfur to determine the amount of elemental sulfur in a fluid.

Any of the herein described test kits, wherein the test kit further comprises a plurality of pipettors. The pipettor volumes can be 1-10 mL, 100-1000 μL, 1-100 μL. The pipettors can be disposable.

Any of the herein described test kits, wherein the test kit further comprises a plurality of cuvettes. Optionally but preferably, each cuvette has a cap such that it can be used for mixing solutions.

Any of the herein described test kits, wherein the test kit further comprises 3-5 containers of pre-weighed elemental sulfur for standards/spikes, wherein a hydrocarbon solvent such as toluene can be added to dissolve the sulfur.

Any of the herein described test kits, wherein the test kit further comprises assorted vials and bottles for liquid containment/mixing/dilution/disposal.

Any of the herein described test kits, wherein the test kit further comprises a timer.

Any of the herein described test kits, wherein the test kit further comprises stands or racks for holding vials, cuvettes, and/or container.

Any of the herein described test kits, wherein the test kit further comprises a portable manual centrifuge for onsite separations/sample prep.

Any of the herein described test kits, wherein the test kit further comprises a portable visible spectrophotometer or LED multi-channel photometer.

Any of the herein described test kits, wherein the test kit contains multiple containers of the caustic chemical, the alcohol, the organic solvent, the hydrocarbon solvent, and/or the caustic solution.

Any of the herein described test kits, wherein the caustic chemical is a strong base.

Any of the herein described test kits, wherein the caustic chemical is a strong base selected from a group consisting of NaOH, KOH, tetrabutylammonium hydroxide, tetramethylammonium hydroxide, tetraethylammonium hydroxide, lithium hydroxide, cesium hydroxide, magnesium hydroxide, lithium methoxide, sodium methoxide, potassium methoxide, lithium ethoxide, sodium ethoxide, potassium ethoxide, lithium propoxide, sodium propoxide, and potassium propoxide.

Any of the herein described test kits, wherein the alcohol is selected from a group consisting of methanol, ethanol, isopropanol, and butanol.

Any of the herein described test kits, wherein the hydrocarbon solvent is selected from a group consisting of gasoline, diesel, kerosene, hexane, benzene, toluene, xylene, heavy aromatic naphtha, mixtures of naphtha and naphthalene, and naphthalene.

Any of the herein described test kits, wherein the caustic solution is a caustic alcohol.

Any of the herein described test kits, wherein the caustic solution comprises a potassium hydroxide, methanol, and toluene.

Any of the herein described test kits, wherein the caustic solution comprises a tetrabutylammonium hydroxide 30-hydrate, isopropanol, and toluene.

Any of the herein described test kits, wherein the caustic solution comprises a mineral hydroxide, an C1-C4 alcohol, and toluene.

Any of the herein described test kits, wherein the caustic solution comprises an ammonium hydroxide, a C1-C4 alcohol, and toluene.

Any of the herein described test kits, wherein the caustic chemical is a mineral or an ammonium hydroxide, wherein the organic solvent is a C1-C4 alcohol, and the hydrocarbon solvent is toluene.

Any of the herein described test kits, wherein the caustic chemical is potassium hydroxide, the organic solvent is methanol, and the hydrocarbon solvent is toluene.

Any of the herein described test kits, wherein the caustic chemical is tetrabutylammonium hydroxide 30-hydrate, the organic solvent is isopropanol, and the hydrocarbon solvent is toluene.

Definitions

As used herein, the term "standard solution" refers to a solution containing a precisely known concentration of an analyte that is used to determine unknown concentrations of the same analyte in other solutions. For the present methods, the analyte is elemental sulfur. The standard solution(s) undergo the same analysis process as the samples, with the same amount of caustic solution being mixed and reacted with the elemental sulfur in the standard solution for the same amount of time before being analyzed by UV-Vis spectroscopy.

A series of at least three standard solutions is needed for comparison with the sample having the unknown concentration of elemental sulfur; however, more standard solutions may be preferred. To prepare the standard solutions, a known amount of elemental sulfur is added to a known volume of fluid with the same matrix profile (i.e. matrix match) as the fluid with the unknown concentration of elemental sulfur. By comparing the absorbance of the sample solution at a specific wavelength to a series of standard solutions at differing known concentrations of the analyte species, the concentration of the sample solution can be found via Beer's Law.

As used herein, the term "fluid" includes both liquids and solids at room temperature that can be solubilized into liquid hydrocarbons.

As used herein, the terms "reaction fluid" and "reaction solution" are used interchangeable to refer to the colored solution formed after the sample fluid containing elemental sulfur and the caustic solution are mixed.

As used herein, the term "peak" in reference to the absorption measurements refer to one or more wavelengths or range of wavelengths having absorbance values in the 90th percentile of the highest observed value. This allows for the use of multiple peaks if the sample's spectrum shows a bi- or tri-modal pattern.

As used herein, the term "low" in reference to the levels or loading of elemental sulfur refers to a concentration of 100 ppm or less of elemental sulfur. The term "high" in reference to the levels or loading of elemental sulfur refers to a concentration of greater than 100 ppm.

As used herein, the term "blank" in reference to solutions and samples mean that there is no analyte of interest in the solutions or samples.

The use of the word "a" or "an" when used in conjunction with the term "comprising" in the claims or the specification means one or more than one, unless the context dictates otherwise.

The term "about" means the stated value plus or minus the margin of error of measurement or plus or minus 10% if no method of measurement is indicated.

The use of the term "or" in the claims is used to mean "and/or" unless explicitly indicated to refer to alternatives only or if the alternatives are mutually exclusive.

The terms "comprise", "have", "include" and "contain" (and their variants) are open-ended linking verbs and allow the addition of other elements when used in a claim.

The phrase "consisting of" is closed, and excludes all additional elements.

The phrase "consisting essentially of" excludes additional material elements, but allows the inclusions of non-material elements that do not substantially change the nature of the invention.

The following abbreviations are used herein:

| ABBREVIATION | TERM |
| --- | --- |
| GC | Gas chromatography |
| IsOH | Isopropanol |
| KOH | Potassium hydroxide |
| LC | Liquid chromatography |
| MS | Mass spectrometry |
| NaOH | Sodium hydroxide |
| TBAOH | tetrabutylammonium hydroxide 30-hydrate |
| UV-Vis | Ultraviolet-Visible |
| XRF | x-ray fluorescence |

DESCRIPTION OF EMBODIMENTS OF THE DISCLOSURE

Figure 1:
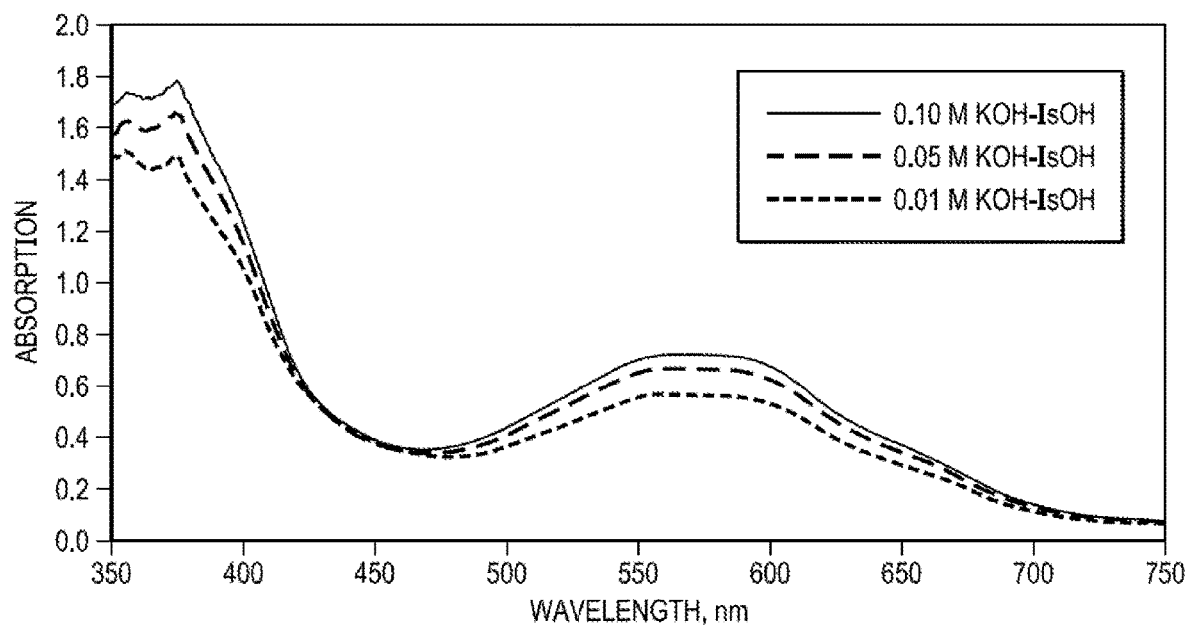
FIG. 1. Absorption scan of 20 g/L elemental sulfur solutions reacted with 0.1, 0.5, and 0.01 M KOH in IsOH. Measurements were taken 1 minute after the addition of the KOH/IsOH to the elemental sulfur solutions.

The disclosure provides novel methods of quantitating the amount of elemental sulfur in a fluid, both in a laboratory setting or in the field, as well as test kits for same. Specifically, a caustic solution is mixed with a sample fluid containing an unknown amount of elemental sulfur, wherein the elemental sulfur reacts with the caustic solution for a known amount of time to form a colored fluid that will be analyzed by a UV-Vis spectrometer to determine the colored fluid's absorbance. The absorbance of the colored reaction fluid can then be compared to the absorbances of a series of standards reacted with the same caustic solution under the same reaction conditions and analyzed by the same spectrometer, to determine the amount of elemental sulfur in the sample fluid. Thus, this robust method is capable of being performed in the field, near the sampling site, or in a laboratory. Once the concentration of elemental sulfur is known, treatment methods can be customized for the sample fluid or system, and the elemental sulfur can be removed or otherwise neutralized or inhibited.

The novel methods can be applied to a variety of fluids, as long as the fluid contains elemental sulfur. The methods are particularly applicable to liquids which have become contaminated with elemental sulfur as a result of being transported in a pipeline previously used to transport sour hydrocarbon streams such as petroleum crudes or solvents used to remediate sulfur deposition (a.k.a. sulfur solvents). The sample fluids can be unrefined hydrocarbon streams, such as raw hydrocarbon condensates or black oil. Alternatively, the sample fluid can be a refined liquid hydrocarbon stream such as gasoline, jet fuel, waxes, and kerosene. In another alternative, the sample fluid is a liquid or emulsion that is used in completion or treatment operations for a reservoir, including oil field solvents such as methanol, monoethylene glycol, triethylene glycol, tetraethylene glycol. In yet another alternative, the fluid is a water and hydrocarbon mixture, or produced water, or a natural gas. In some embodiments, the sample fluid is at least one of, but not limited to, a refined liquid hydrocarbon, an unrefined liquid hydrocarbon (e.g. condensates, black oils), solid hydrocarbons that can be solubilized into liquid hydrocarbons, oilfield solvents (e.g. methanol, monoethylene glycol, triethylene glycol, tetraethylene glycol), and/or combinations thereof.

In more detail, a sample of a fluid containing elemental sulfur can be obtained by conventional means. Depending on the fluid properties and sampling site, at least about 2 mL of fluid is needed for the described methods. Alternatively, about 0.01 mL to 2 mL or about 0.05 mL (50 µL) of the fluid are needed. For fluids with higher elemental sulfur concentrations, less sample volumes are needed.

The standards being compared to the sample fluids are matrix matched to account for background signals during the UV-Vis analysis. The most common method for sample fluid matrix matching is to create standards by diluting the sample fluid into a hydrocarbon solvent (e.g. gasoline, diesel, kerosene, hexane, benzene, heavy aromatic naphtha, mixtures of naphtha and naphthalene, toluene, xylene, and the like), then adding known amounts of elemental sulfur. However, the sample fluid matrix may also be matched by a standard addition approach. In the standard addition approach, the sample fluid is used in a series of standards, where known amounts of elemental sulfur are added. For both matrix matching methods, the original elemental sulfur concentration in the sample fluid can then be extrapolated by linear correlation of the absorbance values.

A caustic solution is added to the sample fluid and standards, and mixed therewith by manual methods such as shaking, swirling, stirring, or vortexing. The caustic reacts with the elemental sulfur to impart a color to the reaction products. The caustic solution does not, however, react with other sulfur containing species such as hydrogen sulfide and disulfide. While the mechanism behind this reaction is not completely known, it is clear that a precipitate is not being formed by this reaction and imparting color to the reaction solution. Further, it is likely that cyclic elemental sulfur species are generating color in response to the addition of caustic.

In some embodiments, the caustic chemical in the caustic solution is a strong base. Any caustic solution that is a strong base can cause a color change with the elemental sulfur, including NaOH, KOH, tetrabutylammonium hydroxide (TBAOH), tetramethylammonium hydroxide, tetraethylammonium hydroxide, lithium hydroxide, cesium hydroxide, magnesium hydroxide, lithium methoxide, sodium methoxide, potassium methoxide, lithium ethoxide, sodium ethoxide, potassium ethoxide, lithium propoxide, sodium propoxide, and potassium propoxide. Preferably, the hydroxides are non-toxic. In some embodiments, the strong base is dissolved in an organic solvent such as methanol, ethanol, isopropanol, butanol, toluene, xylene, DMSO, DMF, propylene carbonate, dioxane, chloroform, diethyl ether, and the like. In some embodiments, the organic solvent is a polar organic solvent. However, the base can also be dissolved in water.

Alternatively, the caustic solution of the present methods can include a caustic alcohol. The use of alcohol as the solvent allows for the flexibility in applying the system to aqueous-based or hydrocarbon-based fluids. The general chemical formula for a caustic in the caustic alcohol is R—O$^-$ and can be stabilized by a countercation such as lithium, sodium, potassium, and titanium. The R group is an alkyl group having 1 to about 8 carbons and can include branching. Exemplary caustic alcohols include, but are not limited to, lithium methoxide, sodium methoxide, potassium methoxide, lithium ethoxide, sodium ethoxide, potassium ethoxide, lithium propoxide, sodium propoxide, and potassium propoxide in methanol, ethanol, isopropanol, or butanol.

The caustic solution can also include a hydrocarbon solvent. In some embodiments, the caustic solution is a caustic alcohol/hydrocarbon solvent mixture, a strong base/organic solvent/hydrocarbon solvent mixture, or a strong base/alcohol/hydrocarbon solvent mixture. Exemplary hydrocarbon solvents include gasoline, diesel, kerosene, hexane, benzene, heavy aromatic naphtha, mixtures of naphtha and naphthalene, toluene, and xylene. Even though some organic solvents are also hydrocarbon solvents, it is preferable that the organic solvent is preferably not the same as the hydrocarbon solvent.

In any of the above solutions, the concentration of the caustic solution is between about 0.0001 and about 19.4 M. Alternatively, the concentration of the caustic is between about 0.01 M to about 0.2 M, preferably between about 0.01 M and 0.1 M, and most preferably is 0.1 M.

The ratio of the caustic solution to the sample fluid or standard solution is about 5:1, but 2:1 or 10:1 may also be possible. Alternatively, about 25 to 50 µL of the sample fluid or standard solution are combined with about 10 mL of the caustic solution.

Once the caustic solution is added to the sample (or standard), the mixture is allowed to react to form a colored reaction fluid. Absorbance measurements of the mixtures are preferably taken between 1 and 15 minutes to obtain precise and reliable measurements, with consistent mixing. To determine the amount of elemental sulfur in the original sample fluid, the absorbance of the sample reaction fluid can be compared to the absorbance of reaction fluids for a series of at least 3, preferably 5 to 12 or more standards having known concentrations of elemental sulfur reacted with the same caustic solution.

A spectrometer such as a UV-Vis is used to determine the absorbance of each reaction solution at a range of wavelengths. The spectrometer can be portable or a benchtop model. The absorbance of the solution is measured by scanning from about 190 to about 750 nm, or from at least 300 to 700 nm. The scan can be continuous or performed in 10 to 15 nm segments. The path length established by the sample cell, also known as a cuvette, can be changed to account for sample fluids with low or high elemental sulfur solutions. For instance, shorter path lengths of about 10 mm can be used for higher elemental sulfur concentrations while longer path lengths of about 50 mm may be needed for lower elemental sulfur concentrations. Once the peak absorbance value(s) over the scanned wavelength range is found, single wavelengths for the remaining samples or standards can be scanned for quantitation purposes.

In some embodiments, other wavelengths besides the ones with peak absorbance can be used. For example, when evaluating a sample with a high concentration sulfur, a non-peak wavelength could allow measurement comparisons without having to dilute the samples.

The absorbance value(s) at the selected wavelength range of each sample is then compared with the absorbance value of the standard solutions at the same wavelength(s). If the absorbance value is too high, the sample solutions and standard solutions may need to be diluted in a hydrocarbon solvent such as gasoline, diesel, kerosene, hexane, benzene, toluene, xylene, heavy aromatic naphtha, mixtures of naphtha and naphthalene, and the like before addition of the caustic solution. The absorbance value should be maintained under 1.3, which equates to 5% light transmission. Values higher than 1.3 decay on a log scale, increasing errors. Thus, the samples solutions may need to be diluted using well-known methods to maintain an absorbance level below 1.3.

Per known methods, a calibration curve can be prepared using the absorbance value of the standard solutions at the wavelengths corresponding to sample reaction fluid's peaks, including any dilutions that need to be factor therein. Once the curve is prepared concentration of the elemental sulfur in the sample fluid can be extrapolated therefrom.

The intensity of the color of the solutions will dissipate over the course of a few hours to a few weeks. However, for purposes of obtaining reliable measurements, the sample should be analyzed within 15 minutes of adding the caustic solution to the sample. Preferably, the samples are analyzed within 5 minutes, and most preferably, at 1 minute. The samples can be measured at some time less than 1 minute, however this time frame may lead to inconsistent mixing and rushing to transfer fluids to the analysis chamber.

After the concentration of elemental sulfur is determined, the user can then customize a treatment method specific to the sampled fluid to remove the elemental sulfur, otherwise treat the fluid, or prevent elemental sulfur formation. Alternatively, the treatment methods may focus on treating the system, such as treating residual sulfur on surfaces of pipelines and other equipment. The fluid can be retested after this removal step, according to the methods described herein.

The herein described methods and kits provide simple and robust methods for quantifying elemental sulfur that require low capital investment and can be applied reliably, and with equal precision, in the field or a laboratory, with real time feedback. Further, the caustic solution has low toxicity relative to mercury or cyanide compounds typically found in other analyses and is more easily handled than other chemicals typically used during the quantification of sulfur.

The presently described methods and kits can be used to analyze sulfur solvents onsite. Sulfur solvents are used to dissolve elemental sulfur deposits out of inaccessible areas like wellbores and subsurface and surface piping without access points, and the like. Sulfur solvent washes are executed by circulating the sulfur solvent through the system until the solvent has dissolved all the elemental sulfur it can at the temperature/pressure conditions selected. Previously, samples have been collected at set time intervals during the wash job and analyzed afterwards, typically by XRF to assess the amount of sulfur dissolved. A well-executed job will have dissolved sulfur at 90+% of solvent capacity. If this target is missed, it cannot be fixed since the solvent, equipment, and people have already moved on to the next job. However, with the currently described methods, the collected samples can be analyzed on using a portable UV-Vis spectrometer to determine if the targeted amount of sulfur has been recovered. This onsite analysis would allow maximum dissolution of the wash job and therefore greater job efficacy.

Another application of this method is testing produced water and sea water. Both types of water dissolve elemental sulfur poorly (<1 ppm), but elemental sulfur can be dispersed in these fluids at higher concentrations. Elemental sulfur concentrations in these fluids has been determined by combinations of known hydrocarbon extraction or centrifugation with hydrocarbon extraction techniques. The resulting hydrocarbon extraction sample can then be analyzed via the caustic alcohol method assisting with corrosion mitigation programs.

In yet another example, the elemental sulfur deposition on corrosion coupons and sectioned oil field piping can be removed from the pieces with a hydrocarbon solvent (typically toluene). Then, this toluene sample can undergo the presently disclosed methods to determine the amount of elemental sulfur that was on the corrosion coupons or piping. Customized treatment programs can then be developed, or modified, to assist with corrosion mitigation programs that utilize these coupons.

The present disclosure also provides for novel test kits that can be used in a field setting but are also applicable to laboratory use as well. In one embodiment, the test kit can have containers, or vials, of premeasured caustic chemicals, organic solvents, alcohol solvents, hydrocarbon solvents, or mixtures thereof (e.g. a premixed caustic solution), as well as vials or containers of premeasured elemental sulfur. The test kit can also have containers or sample cuvettes with caps for mixing, as well as means for measuring out an aliquot of a solution or sample solution. Instructions for using the kit, including how to use and/or mix the caustic chemical, the organic solvent, the alcohol, the hydrocarbon solvent, and the elemental sulfur. Containers for liquid containment, mixing, dilution, and/or disposal can also be included in the test kit.

By providing premeasured amounts of reagents, a user will be able to open the vials of caustic chemicals and organic solvents onsite, transfer to a mixing container or cuvette with a cap, and mix the components to form a caustic solution for reacting with e.g., 50 µL of a sample solution. Alternatively, a vial having a premeasured amount of the caustic solution can be in the kit, allowing the user to open this vial and add the caustic solution directly to the sample solution or vice versa. A selection of caustic and/or organic solvents can be included in the kit to allow the user to prepare a caustic solvent suitable to their sample.

Containers having different concentrations of elemental sulfur in the same fluid matrix as the sample can also be included in the test kit for making a calibration curve in the field. Alternatively, the elemental sulfur and fluid matrix may be in separate containers to allow for the user to customize the concentrations of elemental sulfur in the standard solutions. In some embodiments, a plurality of vials, each with a different, premeasured amount of elemental sulfur can be included in the test kit to allow for a calibration curve to be prepared.

Optional additions to the test kit include a timer, gloves, waste containers, wash solutions for the cuvette if being reused, means for transferring the solutions from the vials to the mixing containers or the cuvette, paper wipes, and a portable UV-Vis spectrometer. Exemplary portable spectrometers include Hach DR1900 and Hach 900. In some embodiments, the test kit has a plurality of pipettors or droppers for transferring solutions. The pipettor volumes can be 1-10 mL, 100-1000 µL, 1-100 µL, and may be disposable.

In other embodiments, the test kit will include protocols for using the test kit, including instructions for generating a calibration curve in field. These protocols will instruct the user to obtain a sample of fluid containing elemental sulfur using conventional means, and to add a known amount to a mixing container. The pre-packaged caustic solutions can then be added thereto and mixed to allow for a ratio of caustic to sample of at least 5:1. Alternatively, the user can prepare the caustic solution on site in the field by opening the containers of premeasured caustic chemical and at least one organic solvent and mixing them together in a separate mixing container to form the caustic solution, then adding the newly prepared caustic solution to the sample. In yet another alternatively, the user can add, at the test site, a hydrocarbon solvent such as toluene to a premixed caustic solution comprising a caustic chemical and alcohol, or a caustic alcohol, to form the caustic solution that will be added to the sample. After almost one minute (e.g. 55-58 seconds) of mixing the elemental sulfur-containing fluid and the caustic, a small amount of the sample can be transferred to a cuvette and placed in a portable UV-Vis spectrometer for scanning. Alternatively, the user can wait up to 15 minutes to scan the sample.

The following examples are included to demonstrate embodiments of the above described methods. These examples are intended to be illustrative only, and not to unduly limit the scope of the appended claims. Those of skill in the art should appreciate that many changes can be made in the specific embodiments that are disclosed and still obtain a like or similar result without departing from the spirit and scope of the disclosure herein. In no way should the following examples be read to limit, or to define, the scope of the appended claims.

EXAMPLE 1

The presently disclosed methods were applied to samples with S8 elemental sulfur, but the method has also been demonstrated on S7 elemental sulfur as well. These samples were mixed with a caustic solution having one solvent alcohol and varying concentrations of base, before being analyzed by a UV-Vis spectrometer.

The concentration of base that would prevent precipitation of particles in the samples, which could interfere with the absorption signal, was evaluated first.

A series of working samples were prepared by dissolving 2 g of a high purity elemental sulfur (S8) in 100 mL of a heavy aromatic naphtha solvent, yielding a concentration of 20 g/L. These S8 samples were then mixed with potassium hydroxide (KOH)/isopropanol (IsOH) solutions in various ratios, and various concentrations of KOH (0.1 M, 0.05 M, and 0.01 M).

Precipitation of solid sulfur particles is a concern as these particles could interfere with the absorption signal. Various sample to caustic solution ratios were tested to determine that mixtures using about 25-50 µL of the S8/solvent solution for every 10 mL of caustic solution were well below the precipitation level for sulfur.

The base content of the caustic solution was also tested. Higher base content results in higher color intensity, which was supported by the results in FIG. 1. Here, 50 L of the S8/solvent solution was combined with 10 mL of the KOH/IsOH having base content of 0.1 M, 0.05 M, and 0.01 M of KOH and shaken vigorously for one minute. Each mixture was then transferred to a 1-inch cuvette, and the absorbance of each mixture was immediately measured as the UV-Vis spectrometer scanned from 350-700 nm. As seen in FIG. 1, the sample mixed with 0.1M KOH/IsOH had a higher absorbance rate than the sample mixed with 0.01M KOH/IsOH.

Figure 2A:
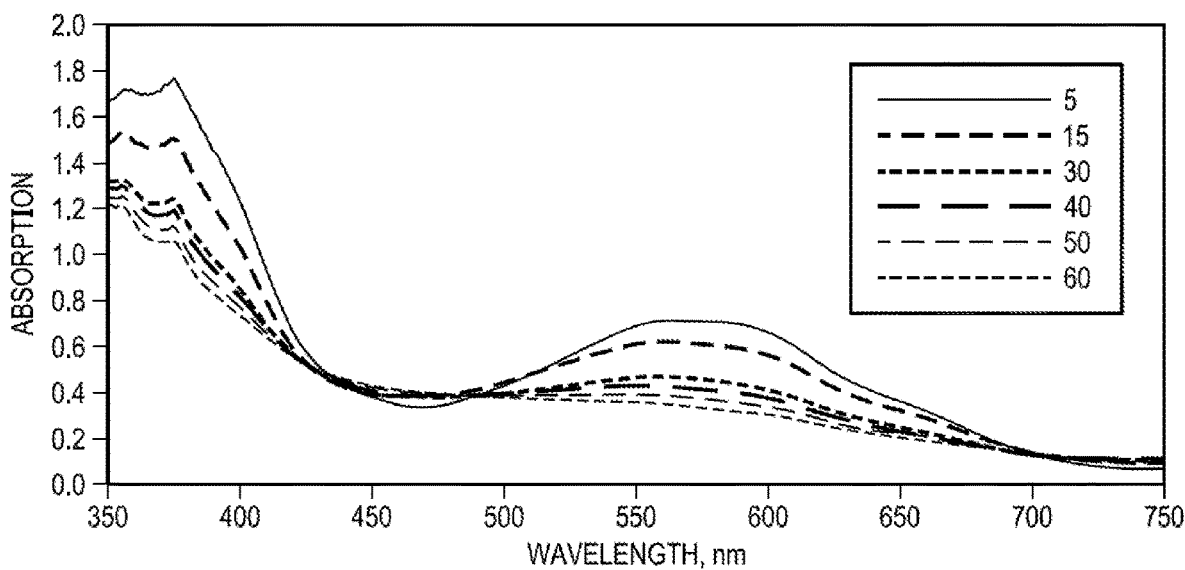
FIG. 2A. Absorption scan of a 20 g/L elemental sulfur solution reacted with 0.1 M KOH in IsOH. Measurements were taken 5, 15, 30, 40, 50 and 60 minutes after the addition of the KOH/IsOH to the elemental sulfur solutions.
Figure 2B:
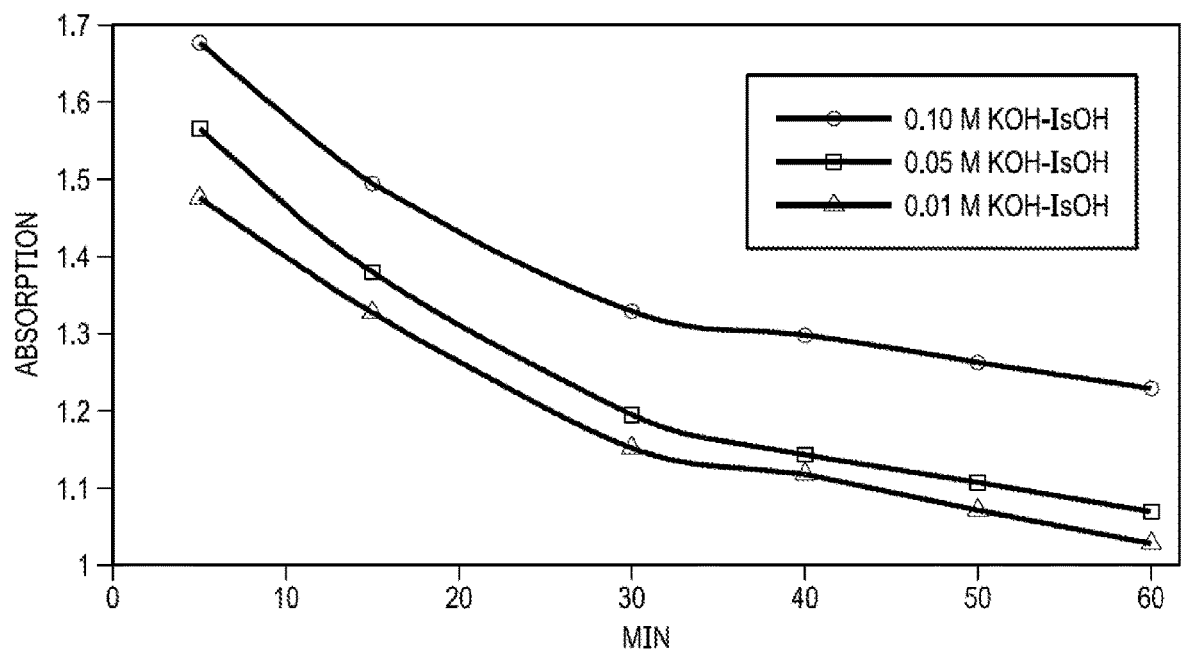
FIG. 2B. Rate of color decline for 20 g/L elemental sulfur solution reacted with 0.1, 0.5, and 0.01 M KOH in IsOH. Measurements were taken 5, 15, 30, 40, 50 and 60 minutes after the addition of the KOH/IsOH to the elemental sulfur solutions.

A concern with the reaction of caustic solution with elemental sulfur is that the color intensity may decline over time. FIG. 2A shows the decrease in absorption from 5 to 60 minutes after mixing 50 µL of the S8/solvent solution with a 0.1M KOH/IsOH solution. Visual inspections also showed a decreased intensity. Similar declines in color were seen with the other caustic solutions. FIG. 2B shows the rate of color decline for KOH/IsOH solutions having a base content of 0.1 M, 0.05 M, and 0.01 M of KOH. It was determined that the samples should be analyzed within 15 minutes of adding the caustic solution, preferably within 5 minutes, and most preferably within about 1 minute of first mixing the caustic solution with the samples.

KOH and IsOH were used in the proof of concept examples described above because the solubility of KOH in IsOH is about 140 g/L. However, different combinations of bases and alcohols can be used. For example, sodium hydroxide (NaOH) has a much more limited solubility in IsOH, so it would not be a preferred caustic base to mix with IsOH. However, it is much more soluble in MeOH.

Addition considerations for the caustic base and alcohol choice include subsequent reactions after the initial analysis. Over the course of a week following the proof of concept work, the samples became cloudy, likely from the reaction of KOH with carbon dioxide in the headspace to make insoluble potassium carbonate. While this salt could be filtered out before analysis on later days, a different base/alcohol combination may prevent the carbonate solubility problem if later analysis is desired. TBAOH does react with carbon dioxide as well to form TBAOH carbonate. However, TBAOH carbonate has a much higher solubility in IsOH than potassium carbonate so it does not precipitate as easily and avoids increasing the turbidity of the solution.

The working samples were re-analyzed using 10 mL of a 0.1 M TBAOH in IsOH as the caustic solution. Measurements were taken at 1, 5, 15, 30, 40, 50 and 60 minutes. The same decrease in absorbance, and corresponding color intensity, were observed. Further, over the course of several days, the solutions were observed for cloudiness or other evidence of precipitation of salts using TBAOH, and none were found. Thus, TBAOH may be preferred for some applications that require testing over the course of days. However, testing is preferably performed within 60 minutes of contacting the caustic with the sulfur-containing solution as this will provide the most consistent and reliable results.

Other observations from the proof-of-concept work include the need to maintain the same sampling volume to limit the absorption values. For the present examples, a high concentration of S8 was evaluated, which resulted in absorbance values as high 1.8. The maximum absorbance value on the UV-Vis scan should not exceed 1.3, which equates to 5% light transmission. Values higher than 1.3 decay on a log scale can increase errors. FIGS. 1 and 2 both showed samples with absorbance values as high as 1.8. To maintain absorption values below 1.3, the sampling volume can be selected to control the maximum absorbance value on the calibration curve. Once a sampling volume is selected, it must be carried through on all standards and samples. If a sample exceeds an absorbance of 1.3, the sample can be diluted 1-5 or 2-4 times to lower the absorbance under the limit of 1.3, with the dilution being accounted for using any other method known in the art. However, most fluids will have a much lower sulfur content, in the range of about <0.1 by mass, and are not expected to show such a high absorbance value, especially after background subtraction techniques are applied.

These proof of concept data showed that it is possible to visually see the change in color after the addition of a caustic solution to a solution containing elemental sulfur. The intensity of the color change can be modified based on the concentration of the base in the caustic solution. However, the color change does dissipate over time. For precision, it is best to analyze the samples within 1 to 15 minutes after combining the samples with the caustic solution. Finally, selection of the base and its solvent are important as some combinations result in the base not being soluble in the solvent or in the base reaction with the sample or its headspace gas to form precipitates that will affect the absorbance measurements.

EXAMPLE 2

Not all elemental sulfur containing fluids are soluble in a single solvent. For example, black oils are not fully soluble in IsOH. As such, the methods were applied to a two-solvent caustic system using toluene and IsOH as the two solvents. As before, 50 µL of a 20 g/L S8 samples were mixed with a 0.1 M TBAOH caustic solution. The solvents for the caustic solution were an 80:20, 60:40, and 40:60 mixture of IsOH and toluene.

Figure 3:
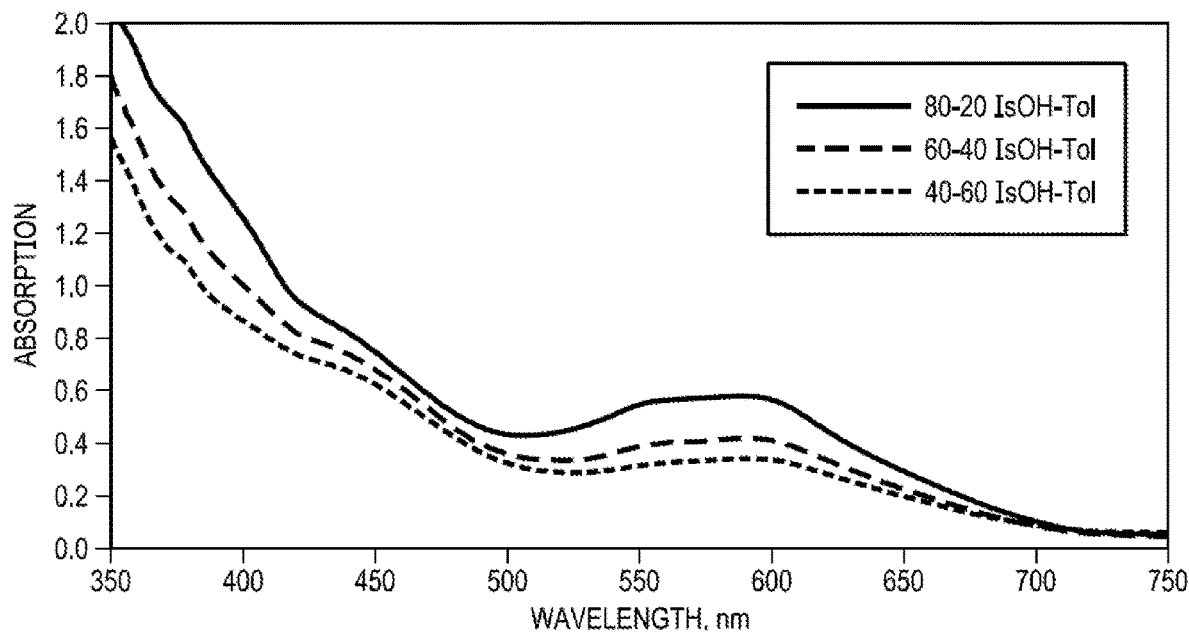
FIG. 3. Absorption scan of 2% (by mass) elemental sulfur reacted with 0.1 M KOH solubilized in solvents with varying amounts of IsOH and Toluene. Measurements were taken 1 minute after the addition of the KOH/IsOH to the sulfur solutions.

The results for this example are in FIG. 3, which show that the use of co-solvents is a viable path to assess elemental sulfur in black oil or other fluids that require a two-solvent system. Toluene did reduce the color intensity as its concentration increased. The mechanism by which toluene reduces the intensity is unknown; however, this reduction in intensity maybe helpful for lowering the maximum absorbance value to 1.3 or less.

Thus, it was found that the elemental sulfur can be reacted with a caustic solution to produced colored solutions capable of being analyzed by UV-Vis spectroscopy. For both methods of analysis, a sample with an unknown concentration of elemental sulfur can be compared to standard solutions having known amounts of elemental sulfur.

The above exemplary use of the methods is intended to be illustrative only, and not unduly limit the scope of the appended claims. Those of skill in the art should appreciate that many changes can be made in the specific embodiments which are disclosed and still obtain a like or similar result without departing from the spirit and scope of the disclosure herein. In no way should the following be read to limit, or to define, the scope of the appended claims.

The following references are incorporated by reference in their entirety.

U.S. Pat. No. 5,199,978, Exxon Res. Eng. Co. (Poirier, et al.) "Process for removing elemental sulfur from fluids," (1991).

US20130149788, Univ. Cornell (Sacks and Kwasniewski) "Assay for quantifying elemental sulfur levels in a sample" (2012).

US20190101519, Saudi Arabian Oil Co. (Oduro), "Quantifying organic and inorganic sulfur components," (2017).

ASTM D2622, ASTM D4292-16e1, ASTM D5453-93, ASTM D5623, ASTM D129-18.

The invention claimed is:

1. An elemental sulfur test kit comprising a storage container comprising:
   a) a first container containing a solution having a known amount of a caustic chemical comprising tetrabutylammonium hydroxide;
   b) a second container containing a known amount of a hydrocarbon solvent;
   c) a third container containing a known amount of an alcohol;
   d) a fourth container containing a known concentration of elemental sulfur; and
   e) a set of instructions for mixing said caustic chemical, said hydrocarbon solvent, said alcohol, and a fluid selected from the group consisting of gasoline, jet fuel, kerosene, condensates, black oils, solid hydrocarbons solubilized in liquid hydrocarbons, produced water, and combinations thereof, and using said known concentration of elemental sulfur to determine an amount of elemental sulfur in said fluid.

2. The test kit of claim 1, said storage container further comprising a plurality of cuvettes and a plurality of pipettes for transferring solutions into the plurality of cuvettes, wherein each cuvette of said plurality of cuvettes has a cap such that said cuvette can be used for mixing at least two of said caustic chemical, said hydrocarbon solvent, said alcohol, and said known concentration of elemental sulfur.

3. The test kit of claim 1, wherein:
   said hydrocarbon solvent is selected from a group consisting of gasoline, diesel, kerosene, hexane, benzene, toluene, xylene, heavy aromatic naphtha, mixtures of naphtha and naphthalene, and naphthalene, and
   said alcohol is selected from a group consisting of methanol, ethanol, isopropyl alcohol, and butanol.

4. The test kit of claim 1, wherein said alcohol is a C1-C4 alcohol.

5. The test kit of claim 1, wherein said hydrocarbon solvent is toluene.

6. An elemental sulfur test kit comprising a storage container comprising:
   a) a first container containing a caustic solution having a known amount of a caustic chemical comprising tetrabutylammonium hydroxide in a known amount of an alcohol;
   b) a second container containing a known amount of a hydrocarbon solvent;
   c) a third container containing a known amount of elemental sulfur; and
   d) a set of instructions for using said caustic solution, said hydrocarbon solvent, and said known amount of elemental sulfur to determine an amount of elemental sulfur in a fluid, said fluid selected from the group consisting of gasoline, jet fuel, kerosene, condensates, black oils, solid hydrocarbons solubilized in liquid hydrocarbons, produced water, and combinations thereof.

7. The test kit of claim 6, said caustic solution comprising tetrabutylammonium hydroxide and C1-C4 alcohol.

8. The test kit of claim 6, said caustic solution being comprising tetrabutylammonium hydroxide and C1-C4 alcohol and said hydrocarbon solvent being toluene.

9. An elemental sulfur test kit comprising a storage container comprising:
   a) a first container containing a caustic solution, said caustic solution comprising tetrabutylammonium hydroxide, a C1-C4 alcohol and a hydrocarbon solvent;
   b) a second container containing a known amount of elemental sulfur; and c) a set of instructions for using said caustic solution and said known amount of elemental sulfur to determine an amount of elemental sulfur in a fluid, said fluid selected from the group consisting of gasoline, jet fuel, kerosene, condensates, black oils, solid hydrocarbons solubilized in liquid hydrocarbons, produced water, and combinations thereof.

10. The test kit of claim 9, said hydrocarbon solvent being toluene.

* * * * *

UNITED STATES PATENT AND TRADEMARK OFFICE
CERTIFICATE OF CORRECTION

PATENT NO. : 12,326,437 B2
APPLICATION NO. : 18/335664
DATED : June 10, 2025
INVENTOR(S) : Jay Locklear and Clinton Crowe It is certified that error appears in the above-identified patent and that said Letters Patent is hereby corrected as shown below:

In the Claims

On Column 18, Line 24 of Claim 2:
"such that it said cuvette can be used for mixing at least two" should read as ----"such that said cuvette can be used for mixing at least two"----

On Column 18, Line 58 of Claim 8:
"8. The test kit of claim 6, said caustic solution being" should read as ----"8. The test kit of claim 6, said caustic solution being"----

Signed and Sealed this
Twelfth Day of August, 2025

Coke Morgan Stewart
*Acting Director of the United States Patent and Trademark Office*